United States Patent [19]

Pastan et al.

[11] Patent Number: 4,545,985
[45] Date of Patent: Oct. 8, 1985

[54] PSEUDOMONAS EXOTOXIN CONJUGATE IMMUNOTOXINS

[75] Inventors: Ira Pastan, Potomac; Mark C. Willingham, Bethesda; David J. Fitzgerald, Wheaton, all of Md.

[73] Assignee: The United States of America as represented by the Secretary, Dept. of Health and Human Services, Washington, D.C.

[21] Appl. No.: 574,173

[22] Filed: Jan. 26, 1984

[51] Int. Cl.[4] .................... A61K 39/00; A61K 39/02; A61K 37/00; A23J 1/06

[52] U.S. Cl. ........................................ 424/85; 424/88; 424/92; 514/2; 514/6; 260/112 B; 260/112 R

[58] Field of Search .................. 424/85, 88, 89, 92, 424/177; 260/112 R, 112 B; 435/240, 241, 875

[56] References Cited

U.S. PATENT DOCUMENTS 4,407,965 10/1983 Yamaihara .......................... 424/85
4,414,148 11/1983 Jansen et al. .................... 260/112 B

OTHER PUBLICATIONS

Schreiber et al., *Proc. Natl. Acad. Sci.*, vol. 78, No. 12, Dec. 1981, pp. 7535–7539, "Monoclonal Antibodics Against Receptor for Epidermal Growth Factor Induce Early and Delayed Effects of Epidermal Growth Factor".

Schreiber, Barbara Mildred, *Diss. Abst.*, vol. 41, No. 12, Jun. 1981, p. 1405b, "In Vitro Toxicity of Antibody *Pseudomona, avergihusu* Exotoxin A Conjugates".

Ostrove et al., *Chem. Abstr.*, vol. 95, 1981, Abstract No. 14648y, "Inhibition of Adenovirus Transferred Cell Cryogenicity with Adeno-Associated Virus".

Trowbridge et al., *Nature*, vol. 294, No. 12, Nov. 1981, pp. 171–173, Anti-Transferrin Receptor Monoclonal Antibody and Toxin–Antibody Conjugates Effect Growth of Human Tumor Cells".

Blythman et al., *Nature*, vol. 290, No. 12, Mar. 1981, pp. 145–146, "Immunotoxins: Hybrid Molecules of Monoclonal Antibodies and a Turin Subunit Specifically Kill Tumor Cells".

Terovanne et al., *J. Immunological Methods*, vol. 35, 1980, pp. 267–275, "Coupling of 5,3-Ketosteroid Isumerase to Human Placental Lactugen with Intramolecular Disulfide Bond Formation, Use of this Conjugate For a Sensitive Enzyme Immunoassay.

Fernandez-Puents et al., *Cell*, vol. 20, No. 3, 1980, pp. 769–776, "Viral Infection Permeabilroes Mammallian Cells to Froteria Toxins".

Fitzgerald et al.; *Cell*, vol. 32, pp. 601–617, (1983).

Fitzgerald et al.; *PNAS*, vol. 80, pp. 4134–4138, (1983).

*Primary Examiner*—Thomas G. Wiseman
*Assistant Examiner*—Robin Teskin
*Attorney, Agent, or Firm*—John S. Roberts, Jr.

[57] ABSTRACT

A method of modifying Pseudomonas exotoxin (PE) with methyl-4-mercaptobutyrimidate is disclosed so that after conjugating the exotoxin to a monoclonal antibody (ab) such as the antibody to the transferrin receptor, the PE-ab conjugate becomes a highly potent immunotoxin suitable for use against human tumor cells. This same method has been used to conjugate PE to epidermal growth factor (EGF) to create a highly potent growth factor-toxin conjugate for use against cells having large numbers of EGF receptors. Also disclosed are the immunotoxin conjugates for Pseudomonas exotoxin coupled to anti-TFR (antibody to the transferrin receptor) and anti-TAC (antibody to the human T-cell growth factor receptor) and to EGF.

16 Claims, 4 Drawing Figures

PSEUDOMONAS EXOTOXIN CONJUGATE IMMUNOTOXINS

UTILITY

The present processes and resulting products which are chemically modified immunotoxins have utility in animals and in human cells in vitro for systematically differentiating and killing cancer cells. This utility has been shown by standard biological tests.

BACKGROUND

Current approaches to cancer chemotherapy and other immunological therapies focus on the use of cell-specific antibodies bonded to immunotoxins in order to kill specific populations of human cells. Ideally, immunotoxins should discriminate to a high degree between target and non-target cells. The critical point, then, is the development of immunotoxins that are highly toxic for specific populations of cells. The present invention details a new class of immunotoxins employing a monoclonal antibody, recognizing a specific human cell receptor, bonded to Pseudomonas toxin. Pseudomonas exotoxin (PE) is modified with methyl-4-mercaptobutyrimidate (MMB) so that, by itself, the toxin exhibits very little toxicity; coupling the modified toxin to a monoclonal antibody, however, transforms the toxin into a highly potent immunotoxin.

Other toxins have been modified in order to produce a suitable immunotoxin. The two best known are ricin toxin and diptheria toxin. However, both of these toxins must be cleaved and the A-chain subunits purified prior to bonding with suitable antibodies. With Pseudomonas exotoxin, the cleavage step is unnecessary. In addition, cleavage of ricin or diptheria toxins into A and B chains removes the portion of the molecule containing residues important for transport into the cytosol of the cell. In contrast, when Psuedomonas exotoxin is modified, no part of the molecule is removed; coupling the exotoxin to a suitable monoclonal antibody produces a very potent cell-specific and easily internalized toxin.

DESCRIPTION OF THE DRAWINGS

FIG. 2 shows the enhancement of PE-anti-TAC toxicity by adenovirus. PE-anti-TAC alone, adenovirus alone (2 μg/ml) or PE-anti-TAC plus adenovirus (2 μg/ml) were added to HUT-102 cells for 4 hr at 37° C. At that time [$^3$H]leucine was added to a final concentration of 3–4 μCi/ml for a further 1 hr. Protein synthesis inhibition was then determined by measuring the reduction in radioactivity incorporated into trichloroacetic acid insoluble material from treated cells versus control cells which received no additions of toxins or virus.

FIG. 3 shows the inhibition of protein synthesis due to PE conjugate. Various concentrations of PE-hybrid toxins ($\Diamond$=PE-cys, $\triangle$=PE-HB21, $\blacktriangle$=PE-HB21 +8×10$^{-8}$ M HB21, $\square$=PE-B3/25, and o=PE-EGF) were added to KB cell monolayers for 16–18 hr at 37° C. Toxin-containing medium was then replaced for 1 hr with fresh medium containing 2 μCi/ml [$^3$H]leucine. Protein synthesis levels were determined and compared to untreated control cells. Control cells incorporated into TCA insoluble material approximately 25,000 cpm/dish.

FIG. 4 shows the enhancement of toxicity due to adenovirus. Various concentrations of PE hybrid toxins ($\Diamond$=PE-cys+adenovirus, $\blacklozenge$=PE-cys, $\triangle$=PE-HB21+adenovirus, $\blacktriangle$=PE-HB21, $\square$=PE-B3/25+adenovirus, $\blacksquare$=PE-B3/25, o=PE-EGF+adenovirus and $\bullet$=PE-EGF) were added to KB cell monolayers for 1 hr at 37° C. in the presence or absence of 3×10$^8$ viral particles/ml. At the end of an hour, the medium was replaced for a further hour with fresh medium containing 1 μCi/ml [$^3$H]leucine. Protein synthesis levels were determined and compared with the appropriate controls.

GENERAL DESCRIPTION OF THE INVENTION

A method has been developed to chemically modify Pseudomonas exotoxin so that the exotoxin can be coupled with growth factors, antibodies, and other biologically active molecules so that this toxin will selectively kill target human tumor cells or other types of cells displaying specific molecules on their cell surface.

PE has recently been conjugated to a variety of monoclonal antibodies recognizing certain human tumors (Cetus Corporation) and to a monoclonal antibody recognizing the human H Type 1 blood group substance [Richert et al. (1983) J. Biol. Chem., 258:8902–8907, and Fredman et al. (1983) J. Biol. Chem., 258:11206–11210]. The toxin-conjugates specifically kill appropriate target cells. PE can now be coupled to a variety of peptides, proteins and growth factors that react with specific receptors on cells. These include sarcoma growth factors, malanocyte stimulating hormone (MSH), somatostatin, glucogon, insulin, transferrin, low density lipoprotein, calcitonin, $\alpha_2$-macroglobulin, and lysine bradykinin. Conjugates with MSH and lysine bradykinin have already been prepared and show some biological activity. Pseudomonas exotoxin is particularly preferable to other toxins (such as ricin or diptheria toxin) because it is easily prepared in large amounts and because humans do not contain the antibodies to neutralize it (as is the case with diptheria toxin) and because it does not have to be separated into subunits before being conjugated.

SPECIFIC DISCLOSURE

Pseudomonas exotoxin (PE) is a known and readily available toxin isolated from *Pseudomonas aeruginosa*. The particular exotoxin used in this invention was the gift of Dr. S. A. Leppla, USAMRIID, Fort Detrick, Md.

PE was chosen for this invention because it acts in the cytosol of the cell to inhibit protein synthesis by catalyzing the enzymatic (ADP-ribosylation) inactivation of elongation Factor Two.

Monoclonal antibodies (Mabs) against the transferrin receptor (anti-TFR) are known and available from the American Type Culture Collection (labelled HB21). These Mabs are propagated as ascites in BALB/c mice and purified by precipitation with 50% saturated ammonium sulfate and affinity chromatography on a column containing *S. aureus* protein A.

Monoclonal antibodies against the T-cell growth factor, anti-TAC, are purified in the same manner as described above for anti-TFR. Anti-TAC is a known and available monoclonal antibody described by Uchiyama et al., *J. Immunol.*, Vol. 126, p. 1393 and p. 1398 (1981).

Epidermal growth factor (EGF) is a well known peptide growth factor, readily available, and extensively studied [Carpenter et al., *J. Cell Biol.*, Vol. 71, p. 159 (1976); Maxfield et al., *Cell*, Vol. 14, p. 805 (1978); and Willingham et al., *Cell*, Vol. 21, p. 67 (1980)].

Pseudomonas exotoxin-monoclonal antibody conjugates (PE-Ab) are constructed either using a disulfide exchange reaction or by forming a thioether bond. For a particular regimen used for a specific Mab, see Examples 1–3. Generally, however, PE is treated with methyl-4-mercaptobutyrimidate (MMB) in order to introduce two thiol groups per molecule of toxin. This step is optimally conducted in 10 mM $KPO_4$ (pH 8.5). Derivatized PE from the above step is then reacted with dithiobis(2-nitrobenzoic acid) (DTNB). Purified antibody is also treated with MMB in order to introduce slightly more than one thiol group per molecule. The treated antibody is then mixed with excess treated PE and allowed to incubate for 2 hrs at 23° C.

Alternatively the antibody can be modified with m-maleimidobenzoyl N hydroxy-succinimide ester (MBS) and the resulting activated antibody reacted with SH-PE-SH to produce a conjugate containing a thioether bond--more stable in an animal environment since it cannot be inactivated by reduction of a disulfide bond.

MMB was selected because it creates a sulfhydryl group when reacted with the amino group present in lysines and at the amino-terminal of proteins. Apparently, it is inactivation of these amino groups that alters PE so that it no longer binds to the PE receptor on cells. Other reagents that react with amino groups may be used in altering PE so that it can be successfully derivitized to antibodies, growth factors, and hormones. These include MBS, N-succinimidyl 3-(2-pyridylthio) proprionate (SPDP), succinimidyl 4-(N-maleimido-(methyl) cyclohexane-1-carboxylate (SMCC) and related agents.

The resulting PE-Ab conjugate is then purified in a multi-step procedure. Typically, 1 ml of conjugate at 3–5 mg/ml is passed over a Sepharose 6B column. Large aggregates in the void volume exhibited low activity and are discarded. The material remaining on the Sepharose 6B column is further purified and separated from unreacted PE by passing the conjugate over a Sephadex G-200 column. The first pool, containing the PE-Ab conjugates used in this invention, includes each PE molecule coupled to one or two antibody molecules. This material reacted with DTNB and then cysteine to derivatize all free-SH groups. Tracer amounts of $^{125}I$-PE may be used to follow the separation procedure. The conjugate is assayed by adding it to tumor cells bearing the appropriate cell surface recognition markers and measuring inhibition of protein synthesis or cell death. The ADP-ribosylating activity of the conjugates is also assayed in cell extracts, usually reticulocyte lysates, using $^{14}C$-NAD as described in Fitzgerald et al., *Cell*, Vol. 32, p. 607 (1983). All experiments were conducted either in vivo on nude mice, or in vitro on human cells in tissue culture.

Target Cells

As indicated in the Background section, this invention couples an exotoxin to a MAB specific for certain cell receptor sites. The type of target cell, then, depends upon the specificity of the monoclonal antibody. Three receptor sites are described in the examples, and the corresponding target cells are described here. However, the invention is not intended to be limited thereby. Growth factor, hormones, monoclonal antibodies, and target cells similar in description to those described herein are included within the ambit of this invention.

KB and Swiss 3T3 cells are maintained as monolayers in Dulbecco's Modified Eagle's Medium (DMEM), supplemented with 10% calf serum (for KB cells) or 10% fetal bovine serum (3T3 cells), and penicillin (50 IU/ml) and streptomycin (50 μg/ml).

HUT-102 and MOLT-4 cells are grown in suspension in RPMI 1640, 10% fetal bovine serum, and penicillin-streptomycin (50 IU/ml—50 μg/ml). The HUT-102 cell line is derived from an adult T-cell leukemia patient and expresses the T-cell growth factor receptor (TCGF). MOLT-4 is a long-term T-cell line that does not bind TCGF and is non-reactive for anti-TAC. Both cells are reactive, however, with antibodies that recognize the human transferrin receptor. Human breast cancer cells (MCF7) and human ovarian cancer cell lines express human transferrin receptors and some cancer specific antigens recognized by monoclonal antibodies supplied by Cetus.

Toxicity Enhancement

The toxicity of the conjugates of this invention is enhanced by the addition of adenovirus type 2 propagated in KB cells grown in suspension culture. The virus is purified by the procedure of Green and Pina, *Virology*, Vol. 20, p. 199 (1963) except that CsCl is used instead of RbCl. Twice-banded virus is aliquoted in 10 ml of sterile tris-saline-30 glycerol and stored in this buffer at −20° C.

The interaction of adenovirus with mammalian cells has been studied most extensively using KB cells. To determine the generality of the adenovirus effect, other human cell lines were assayed for their response to various toxin conjugates in the presence and absence of adenovirus (Table I). Three other human cell lines were sensitive to viral enhancement of toxicity. Two of these were of epithelial origin (A431 and HeLa). The other was a T cell leukemia line. The degree of enhancement and amount of the toxin conjugate necessary to reduce protein synthesis below 50% of normal varied from cell line to cell line. The reason for these variations is not understood but is probably related to such properties as the number of receptors for the conjugate, the number of viral receptors, and the rate of uptake.

It has been shown previously that adenovirus disrupts receptosomes releasing the contents of the vesicle into the cytosol. When the contents of the receptosome included adenovirus and PE-EGF, PE, PE-anti-TFR, PE-anti-TAC, or other toxin conjugates, the inhibition of protein synthesis due to these toxins was markedly enhanced.

TABLE 1

Enhancement of Toxicity in Various Cell Lines due to Adenovirus

| Cell Line | Conjugate | Protein Synthesis % Reduction | |
|---|---|---|---|
| | | Without Adenovirus | With Adenovirus |
| HUT-102 | PE-HB21 (1 ug/ml) | 17 | 65 |
| HeLa S-3 | PE-EGF (0.01 ug/ml) | 0 | 88 |
| A431 | PE-EGF (0.01 ug/ml) | 20 | 80 |
| A431 | PE-HB21 (1 ug/ml) | 27 | 78 |
| Swiss 3T3 | PE-EGF (0.1 ug/ml) | 58 | 67 |
| KB | Ricin A-HB21 (1 ug/ml) | 15 | 86 |

Binding Specificity Studies of PE-Ab Conjugates on HUT-102 and MOLT-4 Cells

Anti-TAC is labeled with tritium by reductive methylation to a high specific activity (7.3 uCi/ug). Anti-TFR is radioiodinated by a modified iodogen procedure [Fraker et al., *Biochem. Biophys. Res. Commun.*, Vol. 80, p. 849 (1978)]to a specific activity of 9 μCi/ug. Peripheral blood mononuclear cells or T-cells are cultured with PHA and anti-TAC binding assayed after 3-4 days. HUT-102 cells, taken directly from tissue culture, are used to assess anti-TFR binding. Both cell types are washed twice in binding medium (RPMI 1640, 1% BSA, 1 mg/ml human IgG, 0.1% azide) prior to antibody additions. The presence of azide allows binding assessments to be made at 23° C. rather than in the cold. Binding experiments are performed in 1.5 ml centrifuge tubes on a rocking platform. From preliminary experiments, equilibrium binding is achieved for both antibodies at approximately 45 min. The results presented represent the average of triplicate samples with a binding time of 60 min. Standard derivations for each point are less than 10% of the mean. From a starting cell concentration of $2\times10^7$ ml, 50 μl is added to the reaction tube, then 20-30 μl of unlabeled antibody (or immunotoxin), and finally 20 μl of radiolabeled antibody. The radiolabeled antibody is kept at a constant concentration (well below half saturation), while the unlabeled antibody is varied over a wide range to determine the concentration of each antibody species that displaces half the labeled antibody. At the end of 60 min. the cells are transferred to a second tube containing PBS, to which sucrose is added to a 1 M concentration. After the appropriate washings, the cell pellet is collected and counted in an appropriate beta or gamma counter.

Toxicity of PE-anti-TAC for HUT-102 and MOLT-4 Cells

Figure 1:
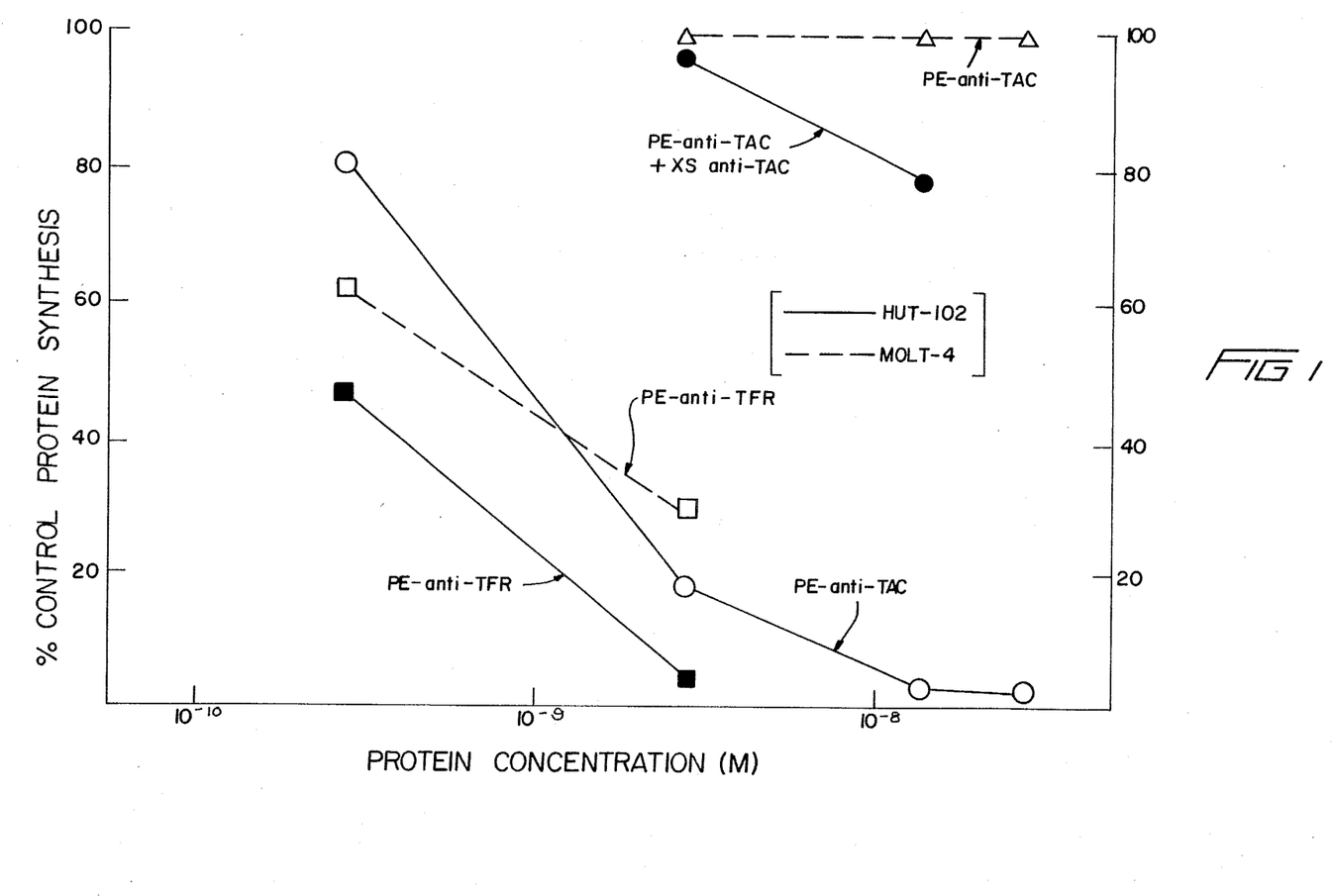
FIG. 1 shows the inhibition of protein synthesis by PE immunotoxin when added to HUT-102 (solid lines) or MOLT-4 (broken lines). Immunotoxins were added to cells in small volumes from stock solutions to give the final concentrations indicated in the specific disclosure. Cells were incubated at 37° C. for 20 hr and [$^3$H]leucine (3–4 μCi/ml, final concentration) was added for a further 1 hr. Control dishes incorporated about 70,000 cpm into trichloroacetic acid insoluble material.

PE-anti-TAC is added to cells at 37° C. and the ability of this conjugate to inhibit protein synthesis is determined after a 20 hr. incubation (FIG. 1). The activity of PE-anti-TAC is compared with a conjugate of PE coupled to an antibody against the transferrin receptor (PE-anti-TFR) by assaying each conjugate on HUT-102 and MOLT-4 cells. Both these cell types contain transferrin receptors, but only HUT-102 cells contain TCGF receptors. Both cell types respond to the PE-anti-TFR conjugate, with the MOLT-4 cell line being 2- to 3-fold less sensitive (FIG. 1). Fifty percent inhibition of protein synthesis occurs at $2.5\times10^{-10}$ M for HUT-102 and $6.5\times10^{-10}$ M for MOLT-4. In contrast, there is at least a 100-fold difference in the response of HUT-102 and MOLT-4 cells to PE-anti-TAC. PE-anti-TAC causes a 50% reduction in protein synthesis at $9\times10^{-10}$ M with HUT-102 cells. There is no detectable reduction of protein synthesis when PE-anti-TAC is added to MOLT-4 cells at concentrations as high as $3\times10^{-8}$ M. Thus, PE-anti-TAC is cytotoxic for cells expressing the TCGF receptor but inactive against receptor negative cells.

Adenovirus-Mediated Enhancement of PE-anti-TAC Toxicity

Figure 2:
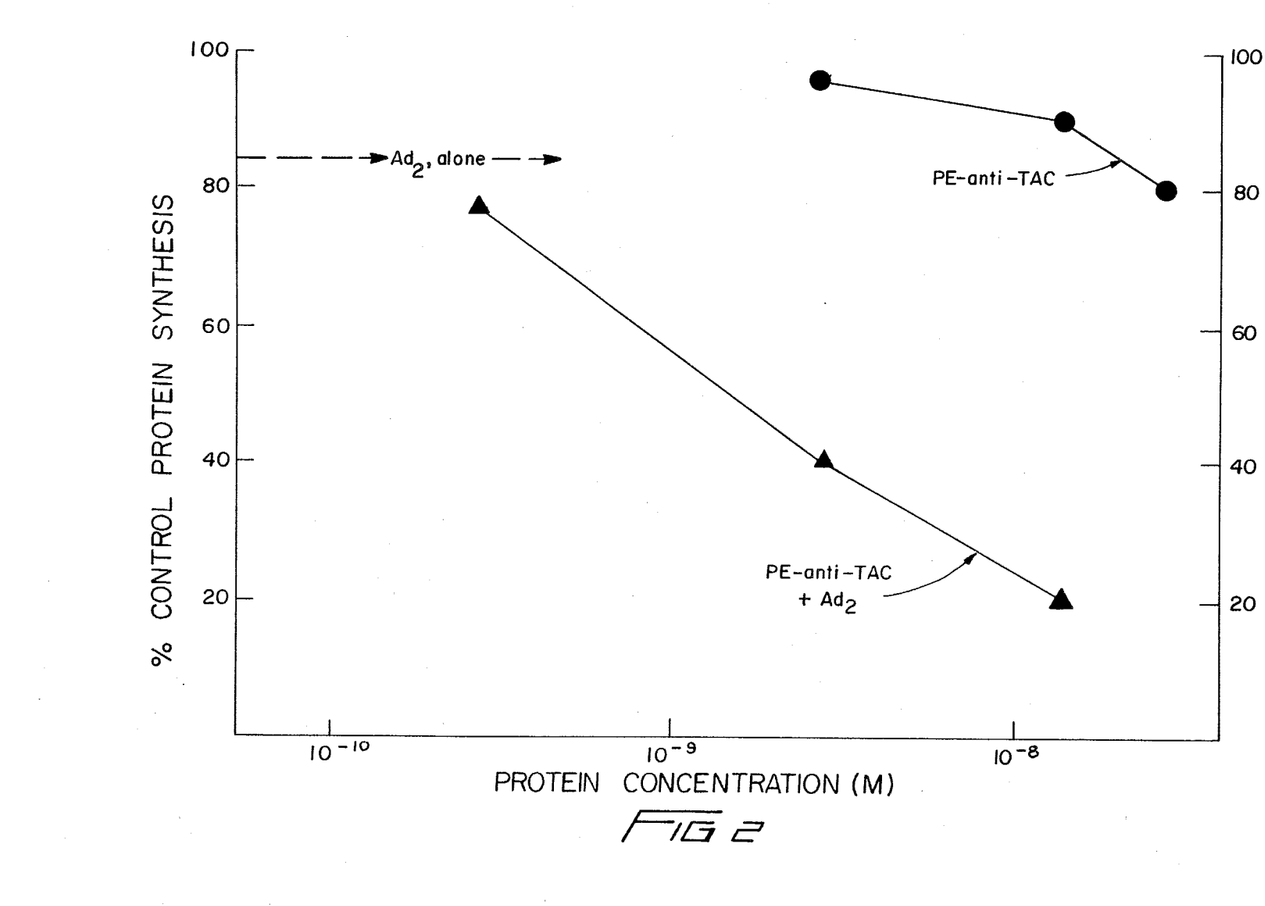

Human adenovirus type 2 enters cells by receptor-mediated endocytosis and begins to escape into the cell cytosol 2-5 min. after it is delivered from coated pits into receptosomes. In human fibroblasts and human KB cells, the virus allows ligands cointernalized with the virus to be released into the cytosol. When the ligand is a toxin or a toxin conjugate, there is an enhancement of toxicity compared with the addition of toxin alone. To determine if the phenomenon occurred in lymphoid cells, adenovirus (2 ug/ml) and PE-anti-TAC are incubated with HUT-102 cells (FIG. 2). As observed with other human cell types, adenovirus enhanced toxicity. Toxicity of PE-anti-TAC is enhanced approximately 50-fold in the presence of adenovirus (2 ug/ml) when compared to the addition of PE-anti-TAC alone. The ability of adenovirus to enhance toxicity also is observed with adenovirus capsids lacking DNA and with U-V treated adenovirus which cannot replicate in human cells.

Toxicity of PE-TFR Conjugate

Toxicity of PE-TFR conjugate, due to entry via the transferrin receptor, is enhanced 100- to 300-fold in the presence of adenovirus.

Figure 3:
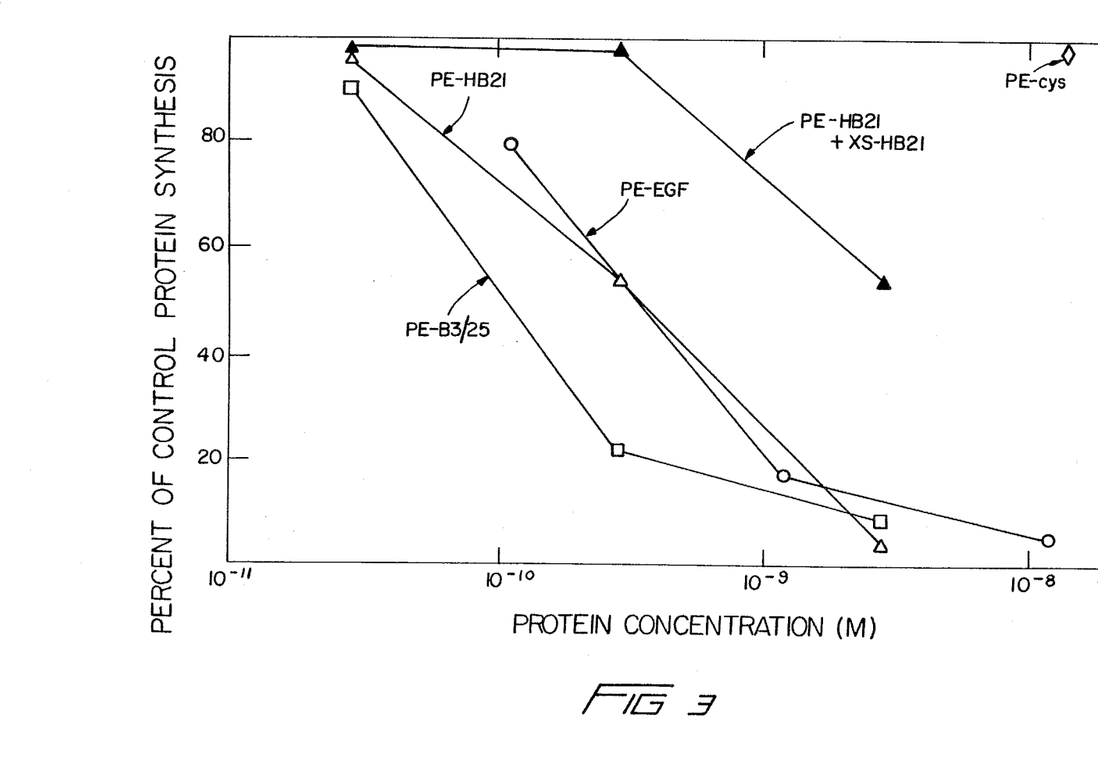

Conjugates of PE coupled to the anti-TFR (HB21) antibody are assessed for toxicity on monolayers of KB cells by measuring levels of protein synthesis (FIG. 3). To do this, various concentrations of the toxin conjugates are added to cell monolayers at 37° C. and incubated for 16-18 hr. To determine levels of protein synthesis, the toxin-containing medium is replaced with fresh medium containing 2 uCi/ml [$^3$H]-leucine and the amount of [$^3$H]leucine incorporated into protein determined after a further incubation of 1 hr. For purposes of comparison, the two conjugates were assayed in parallel with PE-EGF, a conjugate that was previously shown to inhibit protein synthesis in KB cells. the PE-anti-TFR and the PE-EGF conjugates were of similar potency with a TCD$_{50}$ of approximately $3\times10^{-10}$ M.

The specificity of toxicity of the conjugates with the transferrin antibodies was tested in two ways. In the presence of excess unconjugated antibody ($2.8\times10^{-8}$ M), the toxicity of PE-anti-TFR is reduced approximately 10-fold (FIG. 3). Presumably this reduction is due to competition for antibody binding sites. To determine how much activity is due to toxin entry separate from that mediated by antibody binding, PE coupled to cysteine in place of the antibody molecule was assayed for its potency on cells. PE-cysteine (PE-cys) was 500- to 1000-fold less active than PE-anti-TFR or PE-EGF (FIG. 3).

Mouse cells are very sensitive to PE. To evaluate the toxicity of PE-cys more stringently, Swiss 3T3 mouse fibroblasts were used. PE-cys or native PE is added to Swiss 3T3 cells at 4° for 2 hr, the cells are washed extensively, warmed to 37° C. and incubated overnight. PE-cys at $1.4 \times 10^{-7}$ M is not toxic, whereas PE at $1.4 \times 10^{-10}$ M reduces protein synthesis by 40%. Thus, when a binding step at 4° C. is included in the assay, PE-cys is at least a 1,000-fold less active than native PE.

Toxicity of PE-anti-TFR in the Presence of Adenovirus

PE-anti-TFR is added to KB cells at 37° C. for 1 hr in the presence of human adenovirus type 2. After 1 hr. the medium is removed from the cells and replaced with fresh medium containing 2 uCi/ml [$^3$H]leucine. Adenovirus alone at 1 ug/ml viral protein does not reduce the level of protein synthesis. During this short assay period neither PE-anti-TFR at $2.8 \times 10^{-9}$ M nor PE-EGF at $1.2 \times 10^{-8}$ M affected protein synthesis. However, when adenovirus and PE-TFR ($2.8 \times 10^{-9}$ M) are added together, 70 to 80% inhibition of protein synthesis is noted. In various experiments adenovirus at 1 ug/ml enhanced the toxicity of PE-anti-TFR 100- to 300-fold. In comparison, addition of PE-cys ($1.4 \times 10^{-8}$ M) and adenovirus does not result in a significant reduction in protein synthesis.

Toxicity of PE-EGF Conjugate

Figure 4:
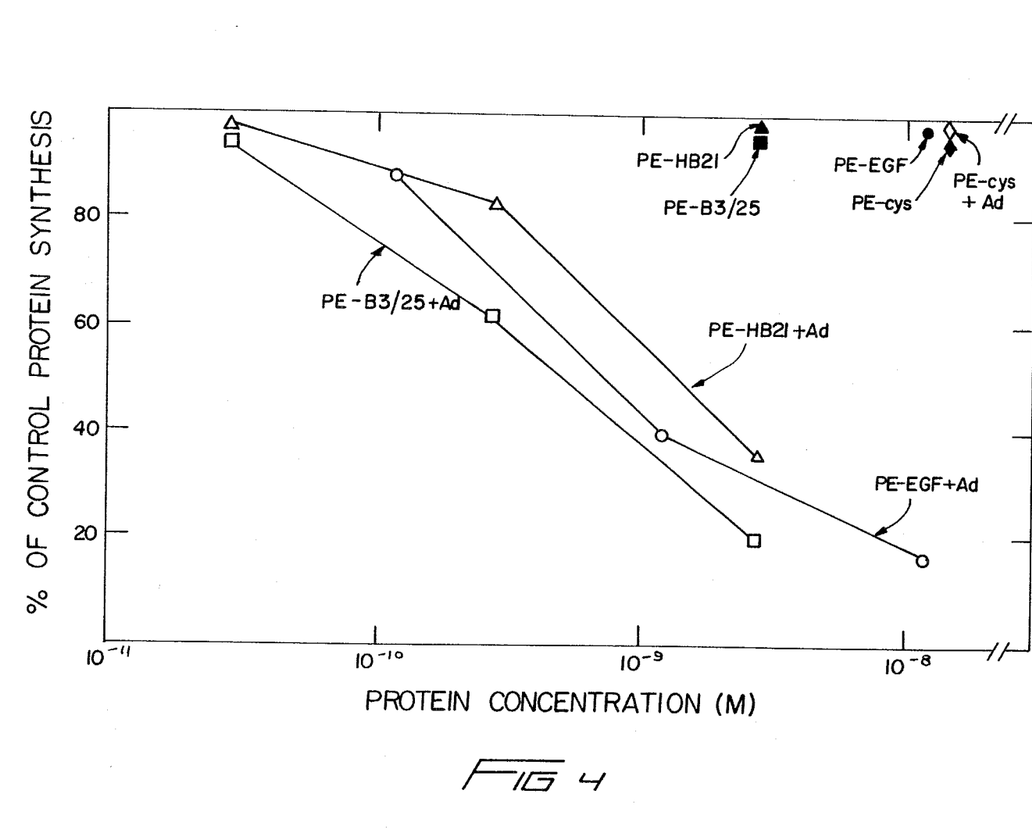

PE and EGF are covalently coupled in the ratio of PE:EGF/1:2. When measured against a standard curve of known toxin concentrations, PE-EGF is found to have retained full enzymatic (that is, ADP-ribosylation) activity (Table 2). As with the native PE, dithiothreitol (DTT) is required for full enzyme activity. However, even in the absence of DTT, the conjugate is partially in an active state. The conjugate is assayed for toxicity on KB cells and compared with native PE (FIG. 4). The hybrid toxin is fivefold more toxic than native toxin. The increased toxicity is abolished in the presence of excess native EGF, indicating that hybrid entry is mediated by EGF receptors.

TABLE 2

| | ADP-Ribosylating Activity of PE, PE-EGF and PE-Au | | |
|---|---|---|---|
| | | NAD Transferred (pmoles/μg/30 min) | |
| | μg/ml | +DTT | −DTT |
| PE | 50 | 140 ± 7.4 | 7.8 ± 0.6 |
| | 25 | 98 ± 4.9 | 5.0 ± 0.2 |
| | 5 | 43 ± 1.9 | 1.1 ± 0.8 |
| PE-EGF | 25 | 98 ± 1.8 | 24 ± 3.6 |
| PE-AU | 25 | 92 ± 6.8 | 41 ± 4.5 |

Results are expressed as pmoles of NAD transferred (in 30 min.) per microgram of EF$_2$.

Protein Synthesis Assay

Inhibition of protein synthesis was used as the index of toxicity. The number of counts per minute in TCA-insoluble material from each dish or, alternatively, the number of counts per minute per microgram of cell protein was determined. Each data point was derived from duplicate dishes with the standard deviation being routinely less than 5% of the mean. Samples were compared with the appropriate controls and results were expressed as percent of control. Each experiment was performed 3 to 4 times.

Adenovirus Enhancement of PE-EGF-Mediated Toxicity

Adenovirus also enhances the toxicity of the hybrid toxin. KB cells have $3 \times 10^4$-$10^5$ receptor sites per cell and $1$-$2 \times 10^3$ PE receptors per cell (unpublished results). Because of the high number of EGF receptors, the uptake of the conjugate, but not necessarily its escape to the cytosol in the absence of adenovirus, should be more efficient than that of native toxin. As seen in FIG. 6, the presence of adenovirus increased the toxicity of the hybrid toxin 10,000-fold. When tested in the presence of excess EGF, this enhancement is substantially diminished, indicating that the hybrid toxin is entering the cell via the EGF receptor. The rate of protein synthesis after incubation with adenovirus plus PE is determined in the absence and presence of excess EGF (10 ug/ml). The same level of inhibition was noted regardless of the presence or absence of EGF. These results further support the case for adenovirus-induced disruption of receptosomes.

EXAMPLES

Examples 1–3, as described in the specific disclosure, incorporate actual values used in the laboratory during synthesis of the desired PE-AB conjugates. The values provided should not be regarded as absolute, but may be varied within experimentally acceptable ranges.

Example 1—PE-anti-TFR Conjugates

PE-anti-TFR conjugates were constructed using a disulfide exchange reaction as described above. Two mg PE was treated with 26 mg methyl-4-mercaptobutyrimidate (MMB) at 37° C. for 2 hr to introduce two thiol groups per molecule of toxin. Derivatized PE was then reacted with 1 mM dithiobis(2-nitrobenzoic acid (DTNB). Purified antibody (2 mg) was derivatized with 1.3 mg MMB for 10 min at 37° C., thereby introducing slightly more than one thiol group per molecule. The derivatized antibody was mixed with a 3-fold molar excess of DTNB-treated toxin and allowed to incubate for 2 hr at room temperature prior to purification and storage or use as a PE-anti-TFR conjugate.

Example 2—PE-anti-TAC Conjugates

PE-anti-TAC conjugates were constructed using the same procedure described in Example 1. Two mg PE were treated with 26 mg MMB at 37° C. for 2 hr. Derivatized PE was then reacted with 1 mM DTNB. Purified anti-TAC antibody (2 mg) was derivatized with 1.3 mg MMB for 10 minutes at 37° C., and then mixed with a 3-fold molar excess of DTNB-treated PE and incubated for 2 hr at room temperature. The conjugate immunotoxin was then stored or used in the toxicity studies described above.

Example 3—PE-EGF Conjugate

PE (0.5 mg) was reacted with 6.5 μg of methyl-4-mercaptobutyrimidate (MMB) at 37° C. for 2 hr in 0.55 ml of 10 mM KPO$_4$ (pH 8.5). NAD was added to a final concentration of 1 mM. (NAD was present to protect the active site of the enzyme.) Derivatized PE was separated from the reaction mixture on a PD10 column, previously equilibrated with 10 mM KPO$_4$ (pH 8.5) and 1 mM NAD. The number of thiol groups introduced by this procedure was assayed by the addition of 20 μl 0.1

M dithionitrobenzoate (DTNB). It was determined from OD absorbance at 412 nM that 2 moles of the thiol group had been introduced per mole of PE. EGF was reacted with MMB to introduce one SH group. Finally, derivatized PE and EGF (in excess) were mixed together and the disulfide exchange reaction allowed to go to completion. The conjugate was separated from free EGF by fractionation on a G-75 column.

EXAMPLE 4

Pseudomonas exotoxin modified with MMB need not be coupled to a monoclonal antibody in order to be biologically effective. At this point, no other toxin can be so modified and remain effective without killing the host animal. For example, less than 1 μg of unmodified toxin is lethal I.P. When Pseudomonas exotoxin was modified and coupled to EGF, nude mice were killed by 20-50 μg of the conjugate. Autopsy showed that they died from liver failure. This is because the liver has a large number of EGF receptors. On the other hand, when Pseudomonas exotoxin was coupled to cysteine by the same chemical reaction, animals given 0.3-0.5 mg of toxin exhibited no signs of toxicity. These experiments show the low toxicity of the chemically modified toxin when coupled to an inert molecule and how it can be coupled to a growth factor to kill receptors containing cells of the liver.

Example 5—Residual Immunotoxin Cell-Binding Activity

Following the coupling of PE to either anti-TAC or anti-TFR, the residual cell-binding activity of each immunotoxin was determined. Only antibody binding was assessed since it has been shown that the chemical coupling of PE to EGF and various antibodies destroyed the toxin's ability to bind to its own receptor. The relative binding activity of PE-anti-TAC compared with anti-TAC was assessed on PHA-stimulated lymphocytes and PE-anti-TFR with anti-TFR on HUT-102 cells. PE-anti-TAC was not assayed for binding activity of HUT-102 cells for technical reasons related to the very large number of anti-TAC binding sites. $^3$H-anti-TAC ($3.5\times10^{-10}$ M) was added to PHA lymphocytes in the presence of various concentrations of either anti-TAC or PE-anti-TAC. The binding of $^3$H-anti-TAC was reduced to a 50% level in the presence of $1.2\times10^{-9}$ M anti-TAC or $2.8\times10^{-8}$ M PE-anti-TAC. In a similar experiment $7.4\times10^{-10}$ M $^{125}$I-anti-TFR was added to HUT-102 cells and displaced to a 50% level by $1.6\times10^{-7}$ M anti-TFR or $1.4\times10^{-7}$ M PE-anti-TFR. The coupling of PE to anti-TAC reduced the binding activity of the antibody by 20-fold, whereas the coupling of PE to anti-TFR had very little effect on its cellular binding.

"Cell binding protein" as used in the specification and claims is defined to mean and include anti-TAC monoclonal antibody, anti-TFR monoclonal antibody, epidermal growth factor, and cysteine.

We claim:

1. A method for the chemotherapeutic alleviation of cancer in animals consisting essentially of injecting a chemotherapeutically alleviating amount of an immunotoxin conjugate which comprises a modified *Pseudomonas exotoxin* (PE) and a modified cancer cell binding protein wherein said PE is modified by treatment with methylmercaptobutyrimidate (MMB) followed by treatment with dithiobis(2-nitrobenzoic acid) and wherein said cancer cell binding protein is modified by treatment with a reagent selected from the group consisting of MMB and m-maleimidobenzoyl N hydroxysuccinimide ester under conditions which effect the formation of a disulfide or thioether bond between said PE and said cancer cell-binding protein.

2. The method of claim 1 wherein said Pseudomonas exotoxin is modified with methyl-4-mercapto-butyrimidate and dithiobis(2-nitrobenzoic acid).

3. The method of claim 1 wherein said cancer cell-binding protein is selected from one member of the group consisting of anti-TAC monoclonal antibody, anti-TFR monoclonal antibody, epidermal growth factor, and cysteine.

4. The method of claim 1 wherein said cell-binding protein is modified with one member of the group consisting of methyl-4-mercaptobutyrimidate and m-maleimidobenzoyl N hydroxy-succinimide ester.

5. The method of claim 1 wherein said chemotherapeutically alleviating dosage is 0.3–0.5 mg.

6. A process for the production of a cancer cell-specific immunotoxin comprising chemically bonding modified Pseudomonas exotoxin (PE) to a modified monoclonal antibody (Ab) wherein PE is modified by treatment with methylmercaptobutyrimidate and dithiobis(2-nitrobenzoic acid) and Ab is modified by one reagent selected from the group consisting of methylmercaptobutyrimidate and m-maleimidobenzoyl N hydroxysuccinimide ester under conditions which effect the formation of a disulfide or thioether bond between said PE and said Ab.

7. The process of claim 6 in which said Pseudomonas exotoxin is modified by treatment with mercaptobutyrimidate under conditions in which 2 moles of sulhydryl are used for every mole of toxin.

8. The process of claim 6 in which said monoclonal antibody is selected from one member of the group consisting of anti-TAC, specific for the human T-cell growth factor receptor; and anti-TFR, specific for a transferrin receptor.

9. The process of claim 6 wherein the chemotherapeutic activity of said toxic protein conjugate is enhanced by administering said toxic protein conjugate in the presence of a human adeno-virus.

10. An immunotoxin conjugate consisting essentially of Pseudomonas exotoxin (PE) bound to a cancer cell binding protein wherein PE is modified by treatment with methylmercaptobutyrimidate (MMB) followed by treatment with dithiobis(2-nitrobenzoic acid) and wherein said cancer cell binding protein is modified by treatment with a reagent selected from the group consisting of MMB and m-maleimidobenzoyl N-hydroxysuccinimide ester under conditions which effect the formation of a disulfide or thioether bond between said PE and said cancer cell-binding protein.

11. The conjugate of claim 10 wherein said cell-binding protein is modified with one member of the group consisting of methyl-4-mercaptobutyrimidate and m-maleimidobenzoyl N hydroxy-succinimide ester.

12. The immunotoxin conjugate of claim 10 wherein said Pseudomonas exotoxin is modified by treatment with methyl-mercaptobutyrimidate and followed by treatment with dithiobis(2-nitrobenzoic acid) under conditions in which 2 moles of sulfhydryl are used for every mole of toxin.

13. The immunotoxin conjugate of claim 10 wherein said cancer cell-binding protein is selected from the group consisting of anti-TAC monoclonal antibody, anti-TFR monoclonal antibody, epidermal growth factor, and cysteine.

14. An immunotoxin conjugate comprising modified Pseudomonas exotoxin (PE) and a modified monoclonal antibody (Ab) wherein PE is modified by treatment with methylmercaptobutyrimidate (MMB) followed by dithiobis(2-nitrobenzoic acid) wherein the monoclonal antibody is modified with a reagent selected from one member of the group consisting of MMB and m-maleimidobenzoyl N hydroxy-succinimide ester under conditions which effect the formation of a disulfide bond or thioether bond between PE and Ab.

15. An immunotoxin conjugate of claim 14 wherein said Pseudomonas exotoxin is modified by treatment with methylmercaptobutyrimidate followed by treatment with dithiobis(2-nitrobenzoic acid) under conditions in which 2 moles of sulfhydryl are used for every mole of toxin.

16. An immunotoxin comprising Pe-B-Ab wherein PE is Pseudomonas exotoxin, Ab is a monoclonal antibody selected from the group consisting of anti-TAC and anti-TFR, and B is a sulfhydryl group bridging agent wherein PE is treated with methyl-4-mercaptobutyrimidate (MMB) followed by treatment with dithiobis(2-nitrobenzoic acid) and Ab is treated with MMB under conditions which effect the formation of a disulfide or thioether bond between said PE and said Ab.

* * * * *